United States Patent [19]
Price

[11] Patent Number: 5,439,593
[45] Date of Patent: Aug. 8, 1995

[54] SOLID PHASE EXTRACTION APPARATUS

[75] Inventor: Thomas E. Price, St. Georges, Del.

[73] Assignee: Hewlett-Packard Company, Palo Alto, Calif.

[21] Appl. No.: 158,179

[22] Filed: Nov. 23, 1993

Related U.S. Application Data

[63] Continuation of Ser. No. 940,020, Sep. 3, 1992, abandoned.

[51] Int. Cl.⁶ .............................................. B01D 15/00
[52] U.S. Cl. .................................. 210/660; 210/236; 210/351
[58] Field of Search ................ 210/350, 351, 266, 282, 210/634, 236, 237, 238, 257, 262, 660, 656

[56] References Cited

U.S. PATENT DOCUMENTS

| | | | |
|---|---|---|---|
| 3,810,545 | 5/1974 | Filz et al. ............................. | 210/198 |
| 4,214,993 | 7/1980 | Forsythe, Jr. et al. ............. | 210/282 |
| 4,358,376 | 11/1982 | Moriuchi et al. .................... | 210/282 |
| 4,655,917 | 4/1987 | Shackelford et al. .............. | 210/198.2 |
| 4,710,289 | 12/1987 | Wermuth et al. ................... | 210/198.2 |
| 4,787,971 | 11/1988 | Donald ................................ | 210/198 |
| 4,871,463 | 10/1989 | Taylor et al. ....................... | 210/161 |
| 4,892,710 | 1/1990 | Wong et al. ..................... | 210/282 X |
| 4,995,976 | 2/1991 | Vermes et al. ................. | 210/282 X |

FOREIGN PATENT DOCUMENTS

| | | |
|---|---|---|
| 0446970A2 | 11/1990 | European Pat. Off. . |
| 0545843A1 | 3/1992 | European Pat. Off. . |
| 2250556 | 11/1973 | France . |
| 2484858 | 4/1981 | France . |
| 9015722.2 | 11/1990 | Germany . |
| WO8912491 | 12/1989 | WIPO . |

OTHER PUBLICATIONS

*Sorbent Extraction Technology*, Analytichem International Inc., Harbor City, CA 90710 (1985).
*Baker-10 SPE Applications Guide Vol. 1*, J. T. Baker Chemical Co., Phillipsburg, N.J. 08865 (1985).
ANSI/HIMA MD70.1 (1983).
*Spe-ed Wiz, The Automated Solid Phase Extractions Sample Preparation System*, Applied Separations Feb. 1989.

*Primary Examiner*—Frank Spear
*Attorney, Agent, or Firm*—Richard Schuette

[57] ABSTRACT

Apparatus for retaining a sorbent bed without permitting voids to be created and that can be readily handled by automated systems is disclosed. A solid phase extraction apparatus is disclosed that is most preferably comprised of a body that contains a sorbent bed and a cap that forms an axial sliding seal with the body. A sleeve is provided to retain the body and create an outside geometry similar to that of a standard glass vial. The sliding seal permits voids in the sorbent bed to be eliminated by axial compressive sealing forces. In a most preferred embodiment, conical sealing surfaces are provided at each end of the disclosed cartridge to facilitate removal of the cartridge after the axial sealing forces are released. The cap and the body are also provided with surfaces compatible with luer fittings, that provide flexibility and permit the use of the invention with existing fluid flow systems.

22 Claims, 3 Drawing Sheets

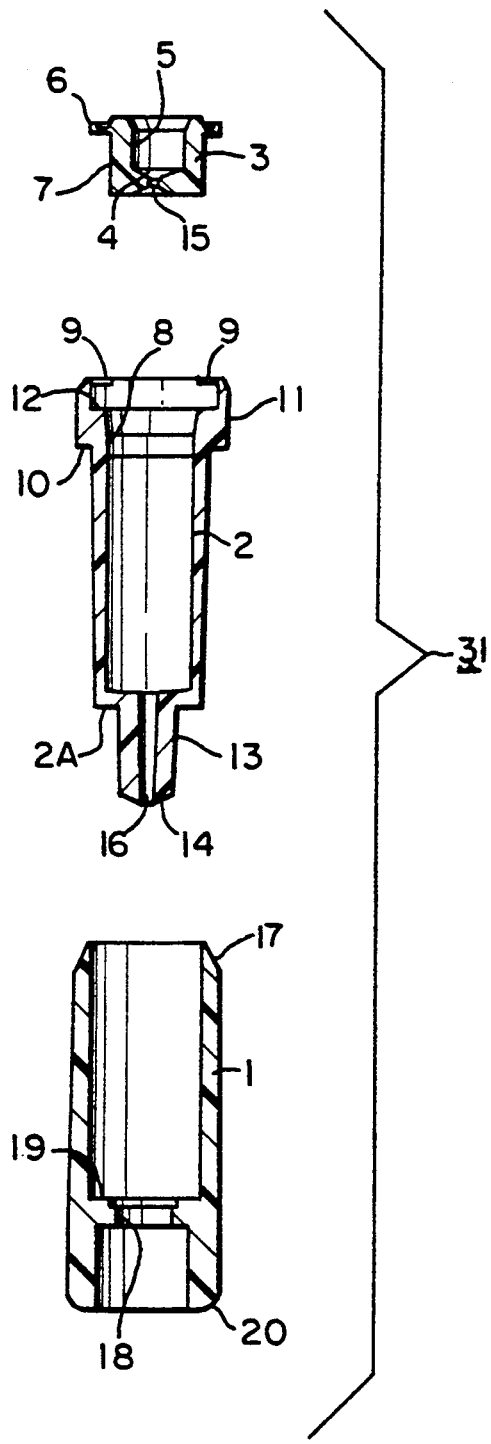
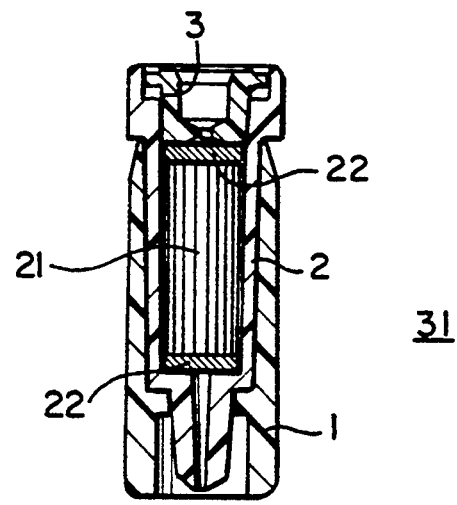
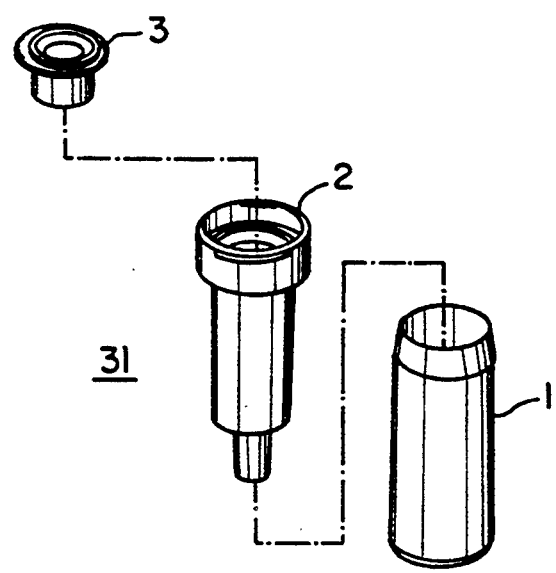
FIG. 1
FIG. 2
FIG. 8

SOLID PHASE EXTRACTION APPARATUS

CROSS REFERENCE TO RELATED APPLICATION(S)

This is a continuation of application Ser. No. 07/940,020 filed on Sep. 3, 1992, now abandoned.

The present invention pertains generally to gas and liquid chromatography, and more particularly to the extraction of an isolate from a sample using a solid-phase sorbent.

BACKGROUND OF THE INVENTION

The use of solid-phase sorbents, e.g., bonded silica, to extract an isolate, usually a chemical compound dissolved or otherwise dispersed in a liquid sample, is known. For example, U.S. Pat. No. 4,710,289—Wermuth et al. discloses a pre-column that has a sorbent packed by a frit. Similar systems are disclosed in *Sorbent Extraction Technology*, Analytichem International Inc., Harbor City, Calif. 90710 (1985) and Baker-10 SPE Applications Guide Vol. 1, J.T. Baker Chemical Co., Phillipsburg, NJ 08865 (1985). It is also known to use disposable columns, similar to the barrels of disposable medical syringes, that retain sorbent between discs of porous material or frits. These columns use a luer-type seal on the bottom, as described in ANSI/HIMA MD70.1 (1983).

However, these prior art systems have certain limitations and disadvantages. Prepared, disposable columns filled with particulate sorbent between frit layers exhibit a tendency wherein the top frit becomes displaced and voids form in the sorbent which, even when extremely small, can distort the results of an extraction and/or solution of the isolate. This problem is recognized by U.S. Pat. No. 4,655,917—Shackelford et al. Moreover, the prior art columns described above do not lend themselves for use in automated systems. The forces needed to disengage the luer taper seal have high variances due to the dimensional tolerances permitted under the above-referenced ANSI standard, and may require rotation about the axis of the luer taper to insure an adequate seal. These requirements do not facilitate handling using conventional robotic "grippers" or other types of automated apparatus. Additionally, modifications to the barrel shape of the syringe columns to allow for robotic manipulation have resulted in significant increase in column volume, thus resulting in reduced storage density within a rack or manipulating device.

Therefore, it would be desirable to create a device that would retain a sorbent bed without permitting voids to be created and that could be readily handled by automated systems. It is thus an object of the present invention to provide a solid phase extraction apparatus that is reliable and easy to use in both automated and manual systems, while providing a high degree of seal integrity and application flexibility. It is also an object of this invention to provide the ability for gas and liquid chromatograph autosamplers to manipulate a solid-phase extraction cartridge in a similar or improved manner to that used to manipulate standard sample vials. Another object of the present invention to provide a cartridge that can be manipulated in a storage density similar to that of standard sample vials. It is a further object of this invention to provide a cartridge that has a seal that requires sealing forces less than or equal to the magnitude required for luer seals, thereby permitting the present invention to be used in automated processes and to provide compatibility with existing semiautomatic and manual processes and apparatus. It is a still further object of this invention to provide means within a cartridge to prevent or severely limit the displacement of a frit disposed on top of the sorbent. Another object of this invention to provide a cartridge that permits a varying internal volume while maintaining a substantially constant external cartridge geometry, so that no handling modifications are necessary to accommodate different sorbent volumes.

SUMMARY OF THE INVENTION

To overcome the limitations and disadvantages of the prior art, and provide for these and other objects, the present invention provides a cartridge for use in a fluid flow system that comprises a body that has a first end for cooperating with a cap to create an axially movable seal between the body and the cap, and a sealing surface at a second end. The cap and the second end of the body each have a substantially axial passageway to permit fluid flow through the cartridge. A sleeve surrounds the body and has an internal mating surface for cooperating with the sealing surface on the body to retain the sleeve on the body. In certain embodiments, however, the sleeve is either permanently affixed to the body or, the body and sleeve are molded as an integral unit. Most preferably, the cartridge is filled with a sorbent and frits are disposed within the body between the sorbent and the cap, and between the sorbent and the second end. In other embodiments, the body is filled with filter material, such as porous fibers or other materials.

One feature of the present invention is the preferred combination of conical surface seals and luer compatible seals that facilitate the automated handling of the cartridge. The cartridge preferably has a conical sealing surface at the distal end of the body for permitting a sealing engagement with the axial passageway, and most preferably, the sealing surface of the body is a male luer-compatible fitting. Similarly, the cap most preferably also uses a conical sealing surface to create a sealing engagement with the axial passageway and has female luer-compatible tapered sealing surface. The internal mating surface of the sleeve is most preferably a female luer-compatible tapered sealing surface, and engages the distal end of the body. The handling of the cartridge by automated systems is further enhanced by providing a lip on the body that forms a juncture with the outer surface of the sleeve to define a point at which the cartridge is grasped.

In another preferred embodiment the body is used as a vessel for use in a fluid flow system, along with the cap, to create an axially movable seal between the body and the cap. A second body is connected to the cap, preferably using luer-compatible fittings, and the first body, that contains sorbent, is connected to a fluid flow system, again using the tapered luer-compatible end of the body. The second body can be filled with a sample and the entire assembly placed with in manual or semiautomatic systems.

The present invention also discloses methods of flowing a fluid through a sorbent contained in a vessel by providing a vessel comprised of a body substantially filled with a material, the body having two ends, a first end for cooperating with a cap to create an axially movable seal between the body and the cap and a second end comprising a sealing surface. A sealing engagement is created between a top probe and an axial passageway in the cap, and between a bottom probe and an axial passageway in the second end. The top probe and the bottom probe are then moved toward each other to create an axial compressive force on the vessel, and the cap slides within the body to compress the material within the body.

BRIEF DESCRIPTION OF THE DRAWINGS

FIG. 1 is an exploded cross-sectional view of an apparatus constructed in accordance with the present invention.

FIG. 2 is a cross-sectional view of an assembly of the apparatus shown in FIG. 1.

FIG. 8 is an exploded perspective view of a preferred embodiment of the apparatus of the present invention.

DETAILED DESCRIPTION OF THE PREFERRED EMBODIMENTS

Figure 3:
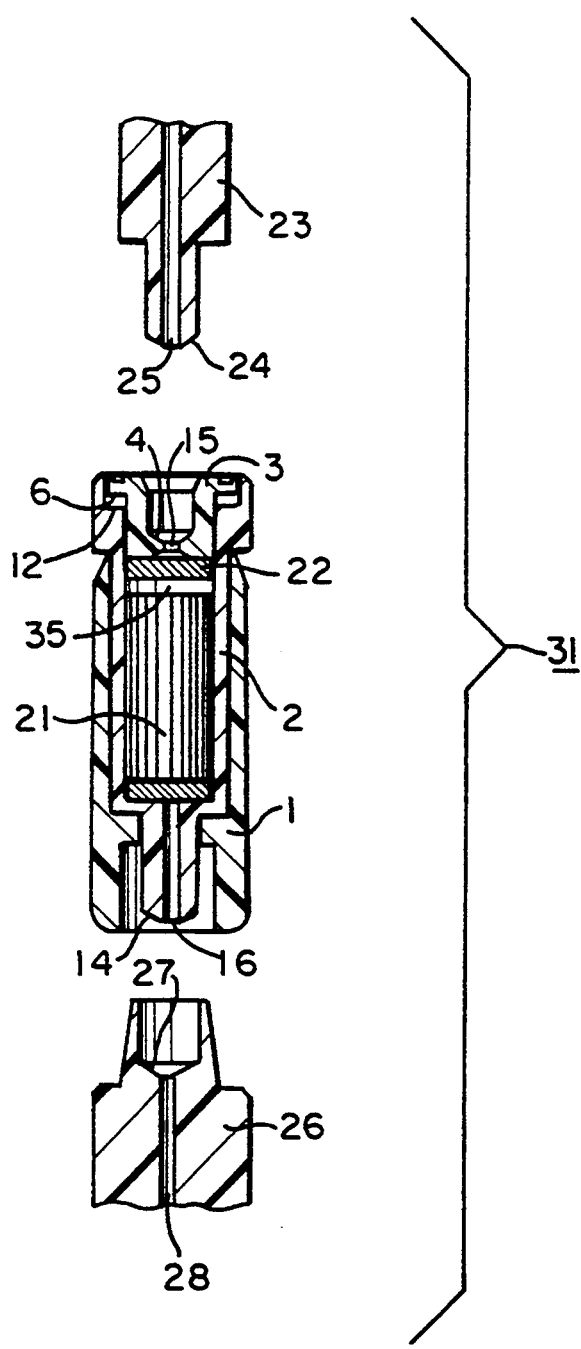
FIG. 3 depicts a cross-sectional view of the apparatus of FIG. 2 prior to its insertion into an instrument.

Referring first to FIG. 8, there is illustrated an exploded perspective view of a preferred embodiment of the apparatus of the present invention. A cartridge sleeve 1 is provided that is most preferably approximately the same external geometry of a conventional autosampler vial. As described in further detail below, a body 2, most preferably for containing a sorbent or other material, is inserted in the sleeve 1 and is locked in place. The assembly is closed using a cap 3 that locks within the body 2. In this embodiment, the present invention thus provides a cartridge 31 whose outside geometry lends itself to be compatible with automated manipulators. As explained below, the cartridge 31 is designed to facilitate the easy making and breaking of the seals in an extraction device or other fluid flow system. Since the external geometry is most preferably formed by a combination of two or more components it is independent of the internal volume, which is defined by the body 2, thereby allowing for different internal volumes while maintaining a common outside geometry. It should be noted, however, that although the cartridge 31 is preferably used with automated apparatus, it can also be used manually.

FIGS. 1 illustrates a cross-section of the components shown in FIG. 8. The body 2 preferably has a substantially cylindrical side wall 8 and closed bottom end 2A that has an axial passageway 16 extending therethrough. The body 2 also has ledges 9 for retaining the cap 3, described below. A lip 10 extends from the cylindrical side wall 8. In a preferred embodiment, a conical sealing surface 14 and self-locking, male, luer-compatible tapered sealing surface 13 are provided on the body 2. For purposes of the present invention, "luer-compatible" is meant to include both true luer fittings and fittings that will cooperate with luer fittings to create a mechanical joint, and/or also create a fluid tight seal. The conical surface 14 ensures that the sealing engagement between the body 2 and a fluid flow system is created by axial compression and thus, upon release of the axial force, there is no resistance to the removal of the body 2 from the fluid flow system. As will be understood by those of ordinary skill, fluid is delivered through the passageway under external pressure or vacuum by an extraction apparatus or other system, not shown in FIG. 1.

The cap 3 has a tapered sealing surface 7 that facilitates sliding the cap 3 into the body 2. Most preferably, a retaining lip 6 on the cap 3 snaps past the retaining ledges 9 in the body 2 to prevent the cap 3 from sliding out of its assembled position. An axially extending passageway 15 is provided in the cap 3 through which fluids pass in order to perform an extraction. At the upper end of the passageway 15 in the cap 3 is a conical sealing surface 4. As explained above with reference to the body 2, the angle of this surface 4 is preferably chosen so that self-locking with mating surfaces will not occur. In general, this angle is preferably less than about 45° from the horizontal. Thus, in a most preferred embodiment, a fluid tight seal is again created between the cap and a fluid flow system by axial compression only. Above the conical surface 4, a self-locking, female, luer-compatible tapered sealing surface 5 is most preferably provided.

The sleeve 1 is adapted to receive the body 2. The sleeve 1 is pressed on to the body 2 until the bottom surface 2A meets an internal mating surface 19 of the sleeve 1. The sleeve 1 is held onto the body 2 by the interference of tapered surfaces 13 and 18 formed on the body 2 and the sleeve 1, respectively. This interference is most preferably formed using a luer-compatible seal. As mentioned above, the cartridge lip 10 formed on the body 2 engages a tapered surface 17 most preferably formed on the sleeve 1.

Referring now to FIG. 2, an assembly of the components discussed above with reference to FIG. 1 is shown. In certain preferred embodiments, a quantity of a sorbent 21 is retained in the body 2 between two porous discs or frits 22. The upper frit is held in place by the cap 3. As mentioned above, the cartridge lip 10 formed on the body 2 extends beyond the tapered upper portion of the sleeve 1 to create a "neck" that is useful as a location at which automated apparatus can grasp the cartridge 31. When the cartridge 31, as shown in FIG. 2 is picked up by a robotic manipulator or other automated handling device, it is handled the same way as a standard two milliliter sample vial. The tapered surface 17 results in the cartridge 31 sliding down while it is grasped until the cartridge lip 10 rests on top of the grasping device, resulting in a consistent carrying position for the cartridge 31. For this reason, a material should be chosen for the sleeve that is relatively rigid, resistive to wear, and that has a low coefficient of friction.

Figure 4:
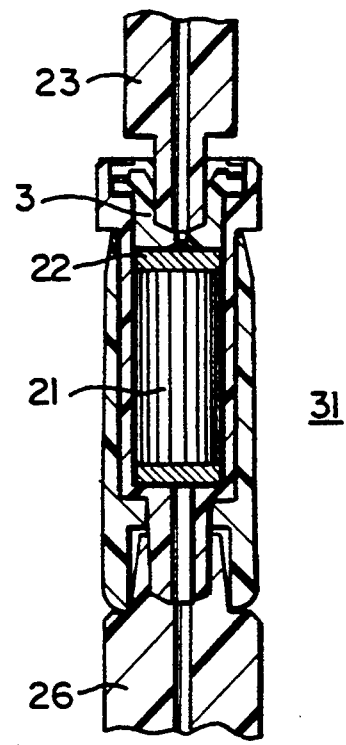
FIG. 4 illustrates the apparatus of FIG. 2 in sealing engagement with an instrument.

As illustrated in FIGS. 3 and 4, the cartridge 31 of the present invention may be brought into communication with a bottom probe 26 or other fitting so that the axial passageway 16 in the body 2 is in communication with an axial passageway 28 in the bottom probe 26. Those of ordinary skill will understand that the bottom probe 26 or similar means are preferably part of the fluid flow system of an extraction apparatus or other device. As explained above, it has been found that sorbent 21 tends to settle over time, resulting in a void volume 35 developing between the top of the sorbent 21 and the bottom surface of the top frit 22, as illustrated in FIG. 3. When the top probe 23, which engages the cap 3, moves between a retracted position shown in FIG. 3 and an axially extended position shown in FIG. 4, it pushes down on the cap 3 which slides axially, causing the frit 22 to move down, filling the void volume 35, as shown in FIG. 4. As long as the maximum axial length of the void volume 35 is less than the axial distance between the cap 3 and the body 2, the void volume 35 can be eliminated. When there is no more relative motion between cartridge parts, the top probe 23 and the bottom probe 26 form a fluid-tight seal using conical sealing surfaces 24,27 that engage the conical sealing surfaces 4,14 of the body 2 and cap 3 while under an axial load. This sealed assembly, shown in FIG. 4, allows fluid to flow through the cartridge 31 and perform an extraction or other operation.

In a preferred embodiment, the top probe 23 is retracted and the cartridge 31 remains in communication with the bottom probe 26, but requires no additional forces other than gravity to remain there. This allows a robotic manipulator or other handling device to remove the cartridge 31. Thus, one aspect of the illustrated preferred embodiment of the present invention is the provision of interior walls in the cap 3 that are sloped and sized such that the top probe 23 does not create a friction fit with the cap 3, and thus requires substantially zero axial force to break the sealing engagement. Similarly, the engagement between the bottom section of the sleeve 1 and the bottom probe 26 does not create a resistive axial force, due to the taper of the bottom probe, as seen in FIG. 4. However, the bottom probe 26 is preferably shaped to act as a "holder" for the cartridge until a manipulator removes it from the fluid flow system.

The combination cone seals and luer-type seals disclosed herein permit the cartridge 31 of the present invention to be used in vacuum systems as well as pressurized systems. This combination of sealing geometry also facilitates self-centering of the cartridge due to the built in tapered sections and defined sealing surfaces described above.

Figure 5:
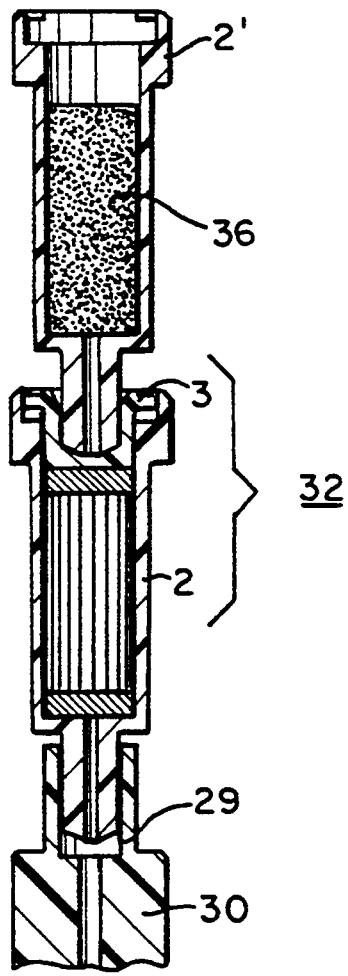
FIG. 5 shows a cross-sectional view of an alternate embodiment of the apparatus of the present invention.

Those of ordinary skill will appreciate that the components described herein are useful in ways other than the assembly shown in FIG. 2; for example, as illustrated in FIG. 5, a sleeveless cartridge 32 is shown. The sleeveless cartridge 32 uses the body 2 and cap 3 described above with reference to FIGS. 1–4, and is most preferably utilized as a manual cartridge embodiment. The sleeveless cartridge 32 is compatible with existing semi-automatic and manual systems. By placing an empty body 2' into a cap 3 that is assembled to a sorbent-filled body 2, an assembly is formed. A sample may be manually placed into the reservoir 36 of the empty body 2' where the sorbent 21 is normally disposed. This complete assembly is connected to a conventional fitting 30, such as a luer fitting that is part of the flow system associated with an extraction apparatus or other instrument. For example, the assembly shown in FIG. 5 can be utilized in a device such as the Speed Wiz ™ sold by Applied Separations of Bethlehem, Penn.

Figure 6:
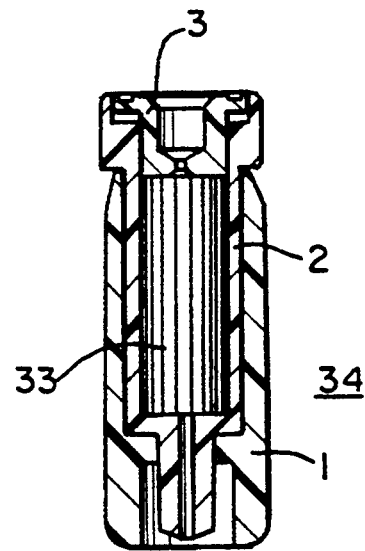
FIG. 6 illustrates a cross-sectional view of another alternate embodiment of the apparatus of the present invention.

Another alternative embodiment of the apparatus of the present invention is illustrated in FIG. 6. In this instance, a material such a porous fiber 33 is placed into a body 2 as described above, thereby creating a filter cartridge 34. The fibers 33 are sealed within the body 2 by a cap 3 and the assembly is slid inside a sleeve 1, as described above. Other types of materials or combinations of different materials could also be used to fill the body 2.

One example of the utility of the present invention is in the case of analyzing urine samples for drugs of abuse testing. Currently, urine samples are taken and prepared for extraction using either semi-automatic or manual methods. The samples are typically manually transferred to a semiautomatic solid phase extraction system where the sample is extracted and the isolate collected in a test tube, evaporated, and transferred to a sample vial. The sample vial is then manually transferred to an autosampler that injects it into gas chromatograph for sample analysis. However, significant improvements in sample throughput can be achieved using the cartridge of the present invention in conjunction with the method described in co-pending and commonly assigned U.S. Patent application Ser. No. 07/702,432 filed May 16, 1991, entitled "Automated Isolate Extraction Using Solid-Phase Sorbent" (Attorney Docket: HP188194A) and the apparatus described in co-pending and commonly assigned U.S. Patent application Ser. No. 870,488, filed Apr. 16, 1992, which is a continuation of Ser. No. 324,362, filed Mar. 15, 1989, entitled "Phantom Row Sample Sequencing" (Attorney Docket: HP 186422) both of which are incorporated herein by reference. In such a system, the samples are processed by extraction using a cartridge 31 as described above, which is automatically transferred to an autosampler and analyzed by the chromatograph, eliminating several steps and a vessel transfer, and permitting the entire process to be automated. Many other semi-automated and manual manipulation tasks can be eliminated or simplified to streamline an operation from the processing a sample to receiving a report on that sample. The present invention also lends itself to many other applications. As shown in FIG. 5, multiple bodies and/or cartridges made in accordance with the present invention can be "stacked" to create a customized flow path. Thus, for example, two cartridges 31 as shown in FIG. 2, but containing different types of sorbent materials can be stacked together. Alternatively, a sorbent cartridge 31 can be stacked with a filter cartridge 34, illustrated in FIG. 6. In any embodiment, the body 2 can be used to retain a sample or any material rather than a sorbent or filter material. The permutations and possibilities are thus almost infinite. In such embodiments, however, there is a small void volume between each body.

Another advantage of the multiple piece cartridges described herein is that different components can be made from different materials. Thus, for manipulation of the cartridge via an autosampler, the material of the sleeve 1 that contacts the autosampler tool is chosen to be wear resistant. On the other hand, the material of the sorbent containing body 2 contacts the sample and thus must be chemically inert relative to the sample, solvents, the sorbent and other materials it contacts. The present invention permits two or more different materials to be used for these functions. Another advantage is that the sleeve 1 is removable and reusable. Thus, different color sleeves can signify different samples or different processing stages, or sleeves of varying outside geometries can be substituted if required by certain processing apparatus. In certain applications, it is necessary to ensure the integrity of a sample and therefore it will be preferable to affix the sleeve to the body so that it cannot be removed without evidence of tampering. For this reason, it may be desirable in certain embodiments to mold the sleeve 1 and body 2 together as one piece or to affix them permanently together.

Figure 7:
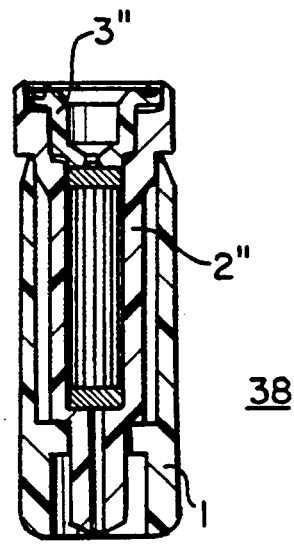
FIG. 7 is a cross-sectional view of an alternate embodiment of the apparatus of the present invention similar to that shown in FIG. 2 but of a different volume.

A further advantage of the multiple piece construction of the cartridge of the present invention is that the volume of the body 2 can be varied within certain limits without affecting the geometry of the sleeve 1. Thus, for example, as seen in FIG. 7, a body 2" can be constructed that is of a smaller diameter than that shown in FIG. 2, while the sleeve 1 and cap 3 remain of substantially the same geometry. This feature provides further flexibility while maintaining compatibility with any robotic manipulators or other automated or semi-automated hardware used to handle the cartridges 31.

It is apparent from the foregoing that many uses can be obtained from the basic cartridge architecture by modifying the cartridge contents or the size and arrangement of the cartridge components. Those of skill in the art will appreciate that a new and improved apparatus for delivering liquid samples has been provided. Unlike the prior art, the sample need not be placed in the cartridge before the sample preparation begins, but instead may be dispensed at a later time into the cartridge. The foregoing exemplary embodiments of the present invention are therefore not limiting. In order to ascertain the true scope of the present invention, reference should be made to the appended claims.

What is claimed is:

1. A cartridge for use in a fluid flow system, comprising a tubular body defining an interior volume, the tubular body having two ends, a first end for cooperating with a cap to create an axially movable sliding seal between the body and the cap, and a second end defining a closed end having an exterior locking surface and an exterior sealing surface, the second end and the cap each having a substantially axial passageway therethrough and each comprising a fluid flow connector, wherein the angle of the sealing surface is less than 45 degrees from a horizontal plane perpendicular to the vertical axis, such that a sealing engagement between the second end and the fluid flow system only exists during the application of axial compression between the second end and the fluid flow system, and upon release of the axial compression, there is no resistance to the removal of the second end from the fluid flow system, the cartridge further comprising a sleeve surrounding the body, the sleeve comprising an internal mating surface for cooperating with the locking surface on the second end of the tubular body to retain the sleeve on the body by a frictional fit.

2. The cartridge of claim 1, further comprising a sorbent substantially filling the interior volume, wherein the cap is slidably mounted within the body and is urged against the sorbent to substantially eliminate any void volumes between the cap and the sorbent.

3. The cartridge of claim 2, further comprising a first frit disposed within the body between the sorbent and the cap.

4. The cartridge of claim 2, further comprising a second frit disposed within the body between the sorbent and the second end.

5. The cartridge of claim 1, further comprising a filter material substantially filling the interior volume, wherein the cap is slidably mounted within the body and is urged against the filter material to substantially eliminate any void volumes between the cap and the filter material.

6. The cartridge of claim 5, wherein the filter material comprises porous fibers.

7. The cartridge of claim 1, wherein the second end of the body has a distal end and the distal end comprises a conical sealing surface for permitting a sealing engagement with the axial passageway.

8. The cartridge of claim 1, wherein the sealing surface of the body is a male luer-compatible fitting.

9. The cartridge of claim 1, wherein the cap further comprises a conical sealing surface for permitting a sealing engagement with the axial passageway.

10. The cartridge of claim 1, wherein the cap further comprises a female luer-compatible sealing surface.

11. The cartridge of claim 1, wherein the internal mating surface of the sleeve is a female luer-compatible sealing surface.

12. The cartridge of claim 1, wherein the sleeve comprises a external surface and the body comprises a lip, whereby the external surface and the lip form a juncture adapted to be grasped by an automated handling device.

13. The cartridge of claim 1, wherein the cap comprises a lip and the body comprises a ledge, whereby the lip cooperates with the ledge to retain the cap within the body.

14. A vessel for use in a fluid flow system having a flow path established therethrough comprising:
a tubular body defining an interior volume,
a cap slidably mounted within a the tubular body and having a first sealing surface for making a sealing engagement with the fluid flow system, the tubular body having two ends, a first, open end for receiving and cooperating with the cap to create an axially movable seal between the body and the cap, and a second, closed end comprising a second sealing surface, the second end and the cap each having a substantially axial passageway therethrough, wherein the angle of the first and second sealing surface is less than 45 degrees from a horizontal plane perpendicular to the vertical axis, such that a sealing engagement between the cap and the fluid flow system and a sealing engagement between the second end and the fluid flow system only exists during the application of axial compression, and upon release of the axial compression, there is no resistance to the removal of the vessel from the fluid flow system.

15. The vessel of claim 14, further comprising a sorbent substantially filling the interior volume wherein the cap is slidably mounted within the body and is urged against the sorbent to substantially eliminate any void volumes between the cap and the sorbent.

16. The vessel of claim 14, wherein the sealing surface of the body is a male luer-compatible fitting.

17. The vessel of claim 14, wherein the cap comprises a female luer-compatible sealing surface.

18. The vessel of claim 14, further comprising a second body wherein the second body comprises a sealing surface that engages the cap.

19. The vessel of claim 14 further comprising a sleeve removably affixed to the body.

20. The vessel of claim 14 further comprising a sleeve permanently affixed to the body.

21. A fluid flow system, comprising:
an inlet port comprising an inlet connector;
a cap having a diameter and a fluid flow passage therethrough and comprising a fluid flow connector having a first sealing surface;
a cartridge comprising a tubular body defining an interior volume, the body having two ends, a first, open end for having a diameter substantially equal to the diameter of the cap for cooperating with the cap to create an axially movable seal between the body and the cap, and a second, closed end comprising a second sealing surface on an external portion of the second end, the second end having a substantially axial passageway therethrough and further comprising a fluid flow connector, the body further comprising an outside surface and an internal mating surface disposed at the second end; and an outlet port comprising an outlet connector, wherein the angle of the first and second sealing surfaces are less than 45 degrees from a horizontal plane perpendicular to the vertical axis, such that a sealing engagement between the cap and the inlet connector, and a sealing engagement between the outlet connector and the second end only exists during the application of axial compression between the inlet and outlet connector, and upon release of the axial compression, there is no resistance to the removal of the second end from the fluid flow system.

22. A method of flowing a fluid through a sorbent contained in a vessel for automatic insertion into a fluid flow system having a top probe for engaging a first end of the vessel and a bottom probe for engaging a second end of the vessel, comprising the steps of:

providing a vessel comprised of a body substantially filled with a material, the body having two ends, a first, open end sealed by a cap having a sealing surface for engagement with the top probe, to create an axially movable seal between the body and the cap and a second, closed end comprising an sealing surface to provide a seal between the vessel and the bottom probe;

aligning the top probe and a substantially axial passageway in the cap;

aligning the bottom probe and a substantially axial passageway in the second end; and moving the top probe and the bottom probe to create an axial compressive force on the vessel, whereby the cap slidably mounted within the body is urged against the material within the body to create a compressive force that urges the top probe into sealing engagement with the cap and the bottom probe into sealing engagement with the second end, wherein the angle of the sealing surfaces is less than 45 degrees from a horizontal plane perpendicular to the vertical axis, such that a sealing engagement between the second end and the fluid flow system only exists during the application of axial compression between the second end and the fluid flow system, and upon release of the axial compression, there is no resistance to the removal of the second end from the fluid flow system.

* * * * *